(12) United States Patent
Xing et al.

(10) Patent No.: US 8,486,171 B2
(45) Date of Patent: Jul. 16, 2013

(54) DRY DUST REMOVAL METHOD IN ORGANIC CHLOROSILANE PRODUCTION

(75) Inventors: Weihong Xing, Nanjing (CN); Zhaoxiang Zhong, Nanjing (CN); Nanping Xu, Nanjing (CN)

(73) Assignees: Nanjing University of Technology (CN); Nanjing Jiusi High-Tech Co., Ltd. (CN)

( * ) Notice: Subject to any disclaimer, the term of this patent is extended or adjusted under 35 U.S.C. 154(b) by 0 days.

(21) Appl. No.: 13/381,108

(22) PCT Filed: Feb. 4, 2010

(86) PCT No.: PCT/CN2010/070512
§ 371 (c)(1),
(2), (4) Date: Dec. 28, 2011

(87) PCT Pub. No.: WO2011/094938
PCT Pub. Date: Aug. 11, 2011

(65) Prior Publication Data
US 2012/0285194 A1    Nov. 15, 2012

(51) Int. Cl.
*B01D 45/00* (2006.01)
*C01B 33/08* (2006.01)
*F27B 15/14* (2006.01)
*G01D 11/26* (2006.01)
*G01N 1/00* (2006.01)

(52) U.S. Cl.
USPC ............. 55/342; 423/342; 422/146; 422/119

(58) Field of Classification Search
USPC ..................... 55/342; 423/342; 422/146, 119
See application file for complete search history.

(56) References Cited

U.S. PATENT DOCUMENTS

| 4,610,858 A * | 9/1986 | Yamada et al. ............... 423/342 |
| 2004/0050773 A1 * | 3/2004 | Neumann et al. ............. 210/490 |
| 2011/0229398 A1 * | 9/2011 | Troll et al. ..................... 423/342 |

FOREIGN PATENT DOCUMENTS

| CN | 1438226 | 8/2003 |
| CN | 101148453 | 3/2008 |
| CN | 101337974 | 1/2009 |

OTHER PUBLICATIONS

International Search Report; PCT/CN2010/070512; International Filing Date: Feb. 4, 2010; Nanjing University of Technology et al.; 4 pages.

* cited by examiner

*Primary Examiner* — Amber Orlando
(74) *Attorney, Agent, or Firm* — Schmeiser, Olsen & Watts, LLP

(57) ABSTRACT

Dry dust removal method in organic chlorosilane production is provided, in which the detailed steps are as follows: delivering high-temperature flue gas (a) from fluidized bed reactor (I) into inorganic film cross-flow filter (E) to remove dust for the first time; delivering the concentrated dust gas (c) trapped by inorganic film cross-flow filter (II) into bag filter (III) to remove dust for the second time; returning the gas mixture (f) of passing through bag filter (EI) to the air intake of inorganic film cross-flow filter (II); condensing the residual clean gas (b) from the osmotic side of inorganic film in condenser (A), and then rectifying in rectifying column (B) to separate the products of chloromethane (g) and methyl chlorosilane (h) to obtain the product of methyl chlorosilane (h); returning chloromethane to fluidized bed reactor to take part in reaction; retreating the dust (e) trapped by inorganic film cross-flow filter and bag filter, and then returning it to fluidized bed reactor (I) to take part in reaction.

6 Claims, 1 Drawing Sheet

DRY DUST REMOVAL METHOD IN ORGANIC CHLOROSILANE PRODUCTION

TECHNICAL FIELD

This invention is a kind of dust removal method of gas, which is especially involved in a dry dust removal method in organic chlorosilane production and is used in the methyl chlorosilane synthesis process that uses chloromethane and silicon powder as raw material.

BACKGROUND

Organic silicon compound is generated when silicon powder reacts with chloromethane with the action of catalyst. Organic silicon is not only a kind of new-style material itself, but also provides a new material base and technical guarantee for the development of relevant industry fields. High development speed is always kept in organic silicon industry, the yield of organic silicon (converting into siloxane) in China was up to 200 kt/a in 2006.

The gas mixture generated from the reaction of silicon powder and chloromethane with the action of catalyst is a kind of mixture that contains several kinds of silane gas and dusty raw material. It needs to remove dust from gas mixture during the production of organic silicon.

Currently, dry and wet dust removal equipment is mainly used in organic silicon plant, namely, several sets of serial cyclone separator dust-removal systems and venturi dust-removing system are used to effectively separate solid dust from the gas-phase products in a fluidized bed reactor. The concrete process flow is as follows: gaseous solid-phase reaction occurs between chloromethane and silicon powder in a fluidized bed reactor to generate mixed monomer methyl chlorosilane; the gas phase product generated from the reaction is removed of dust by means of cyclone; the separated solid is discharged into a dust box after being sent into a dust collector; After being separated with cyclone separator, the reaction gas that contains a small amount of dust enters the venture scrubber, where mixed methyl chlorosilane monomer is used as cleaning solution for wet dust removal; the gas that has been removed of dust enters the fractional condenser after passing through a gas evaporator and buffer tank; the cooled product enters degassing column, and finally methyl chlorosilane is obtained.

Some companies also use the combination of dry bag-type dust collector and water washing to remove the solid-phase dust from gas mixture. However, traditional cyclone dust collector and bag-type dust collector cannot completely remove the small-sized dust from gas mixture, and so it needs to use washing method to further remove dust from gas mixture. As a result, the entire process is complicated, and dust removal by water washing will consume a great amount of industrial water, and wastewater release will impact the environment.

An organic chlorosilane wet dust removal process has been announced in China's patent number CN1438226A. This process replaces the traditional dry dust removal process with a continuous wet dust removal method that uses organic chlorosilane as a cleaning solution; there are no dust removal steps of cyclone separator or bag-type collector during an entire process. However, the slurry of this dust removal method contains about 60% of organochlorosilane; in this case, it is difficult to extract the solid matter from the scullery, and the consumption of organic chlorosilane is high.

A kind of dry dust removal method and unit for organic chlorosilane gas is introduced in China's patent number CN101148453A. In this method, the DIA-SCHUMALITH 10-20 porcelain filter element produced by PALL Company is used to remove dust from dust-containing gas mixture, and the purified organosilane gas mixture gets into the next working procedure. DIA-SCHUMALITH 10-20 filter element is formed by way of binding porcelain and carborundum. Large-pored carborundum crystal lattice is used as a rigid and stable structure to support film; the film is the part that really plays filtering role, and is consisted of multi-aluminum andalusite, with thick of 100-200 μm and bore diameter of about 10 μm. However, this method is of terminal-type filtering method, and filter cake tends to accumulate on film surface, this would cause flow to rapidly decrease, and filtration resistance to increase, the frequent backwash for maintaining flow brings very high stress on the strength of film.

SUMMARY

The purpose for this invention is to provide a kind of dry dust removal method in organic chlorosilane production that has a simple process, high dust-removal efficiency and low environment pollution. In this method, inorganic film cross-flow filter is used to accomplish the separation of solid and gas and to simplify existing process so as to overcome the disadvantages of wet dust removal method such as complicated process and environmental pollution due to wastewater produced in water washing process.

Technical proposal of this invention: a kind of dry dust removal method in organic chlorosilane production; the concrete steps are as follows:

A) The high-temperature flue gas generated in a fluidized bed reactor is first delivered to inorganic film cross-flow filter with air compressor to remove dust for the first time.

B) The concentrated dust gas trapped by inorganic film cross-flow filter in the above-mentioned steps enters the bag filter to remove dust for the second time; the gas mixture purified with the bag filter returns to the inorganic film cross-flow filter via a fan.

C) The clean gas mixture passing through the inorganic film cross-flow filter enters the condenser for condensation, and then enters rectifying column to separate chloromethane and methyl chlorosilane; chloromethane returns to the fluidized bed reactor to participle in reaction.

D) The dust trapped by the inorganic film cross-flow filter and bag filter returns to the fluidized bed reactor to participate in reaction.

The foregoing inorganic film cross-flow filter is consisted of casing, film filtering element, upper figured plate and lower figured plate, of which the upper and lower figured plates are placed in the middle of the casing, and film filtering element is placed between the upper figured plate and lower figured plate; high-temperature flue gas inlet is provided at the top of inorganic film cross-flow filter, and concentrated dust flue gas outlet is provided at the bottom of the filter; clean gas outlet and blowback gas inlet are provided between the upper figured plate and lower figured plate; high-temperature flue gas enters the inorganic film filter for cross-flow filtration via the high-temperature flue gas inlet; the clean gas passing through the inorganic film cross-flow filter is drained out via the clean gas outlet; the concentrated dust gas trapped by the inorganic film filter enters the bag filter via the concentrated dust gas outlet.

The above-mentioned inorganic film cross-flow filter is provided with the connection of the blowback device; the blowback gas (d) is the clean gas passing through the inorganic film filter and compressed with the clean gas compressor, and enters the inorganic film filter for blowback cleaning via the blowback gas inlet. When film flux is decreased to 40-60% of initial flux, the clean gas at the outlet of the inorganic film filter is automatically used to intermittently blow back the film separator; in this way, the filter cake attached on the film surface falls off and sinks down to the bottom of the separator, thus effectively preventing film pollution.

The high-temperature flue gas in step A is preferred to flow into the inorganic film cross-flow filter in parallel with film surface; when the gas enters the inorganic film cross-flow filter, the film-crossing pressure is controlled at 0.01 MPa-1 Mpa, and the flow rate on the film surface is 1 m/s-100 m/s.

The film filtering element as described in the inorganic film cross-flow filter section is preferred to be tubular film made of ceramics and metal material; the mean pore diameter of the film is 0.02 μm~50 μm, and the diameter of film channel is 3-100 mm.

The above-mentioned ceramic material is preferred to be aluminum oxide, zirconium oxide or silicon carbide; the forgoing metallic material is of stainless steel, FeAl alloy or FeCrAl alloy, etc.

The separation process of this invention is that, the high-temperature flue gas leaving the fluidized bed reactor is sent to the inorganic film cross-flow filter with air compressor to remove dust for the first time; the concentrated dust gas trapped by inorganic film cross-flow filter enters the bag filter to remove dust for the second time; the clean leaving the inorganic film cross-flow filter is used as blowback gas for intermittently blowing back the inorganic film cross-flow filter after being compressed with compressor; the remaining purified gas is condensed and rectified, and then is used to separate chloromethane gas and methyl chlorosilane, and the obtained product methyl chlorosilane and chloromethane gas return to the fluidized bed reactor to participate in the reaction; the dust trapped by the inorganic film cross-flow filter and bag filter return to the fluidized bed reactor to participate in the reaction.

The inorganic film in the invention has high mechanical strength, good stability, and is high-temperature resistant, thus effectively removing the dust of gas mixture.

Favorable Effect:
(1) On the base of producing methyl chlorosilane with a direct method, this invention process does not change the original reaction condition, and inorganic film is used to separate the small-sized dust of organic gas mixture so as to complete the separation of gas and solid in continuous production.
(2) The process of this invention is simple, and blowback gas needs not to be additionally heated.
(3) There is no dust-removing step by way of wet washing in this invention, and so the consumption of industrial water is little, and there is no wastewater drain, thus minimizing environmental pollution.
(4) The dust-removing rate in this invention is high, and separation efficiency exceeds 99.8%.

Figure 1:
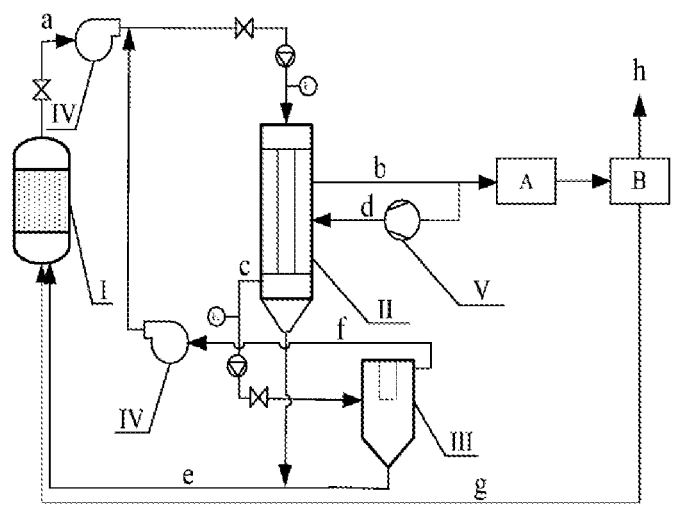
FIG. 1 shows the dust separation flow chart during the synthesis of methyl chlorosilane using direct method in this invention, where I—fluidized bed reactor; I—inorganic film cross-flow filter; III—bag filter; IV—fan; V—compressor; A—condenser; B—rectifying column.

Where, 1—concentrated dust gas outlet; 2—shell; 3—film filter element; 4—high-temperature flue gas inlet; 5—upper figured plate; 6—clean gas outlet; 7—connection of blowback device; 8—lower figured plate; 9—dust charge port;

DESCRIPTION OF EMBODIMENTS

Example 1

The following is the detailed description of the invention in combination with the attached diagrams:
A) The high-temperature flue gas (a) leaving the outlet of reactor (I) is sent to the inorganic film cross-flow filter (II) for separation with the effect of a centrifugal fan (IV). The inorganic film cross-flow filter (II) is the product of Nanjing Jiusi High-tech Co., ltd, and the film filter element (3) is of 4 pieces of zirconia film with the pore diameter being 0.2 μm, channel quantity 19, inner diameter of channel 6 mm, cross-flow velocity 30 m/s, film-crossing pressure differential 0.1 MPa; the dust content of the gas at the feed side is 0.9308 g/m$^3$; the flux of the film tube at the beginning of filtering is 51.5 m$^3$/m$^2$·h; the dust content of the gas at the penetration side of the film tube is 1.1 mg/m$^3$. Concentrated dust gas (c) trapped by the inorganic film filter (II) flows into the bag filter (III).

Figure 2:
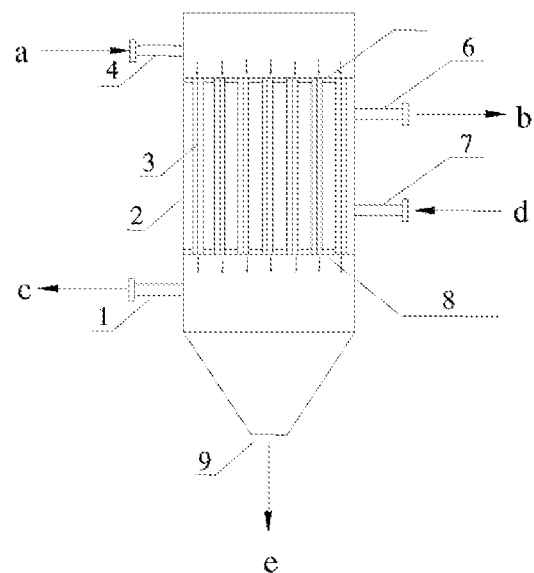
FIG. 2 shows the structural schematic diagram of the inorganic film cross-flow filter in this invention.

In this invention method as shown in FIG. 2, the high-temperature flue gas (a) that contains solid particle of silicon powder and catalyst copper powder enters the inorganic film cross-flow filter (II) via high-temperature gas inlet (4), and then it enters the film filter element (3). The penetrating gas vertical to the flow direction of the former gas mixture is drained through the clean gas outlet (6). The trapped dust-rich gas (c) is drained out of the filter (II) via the outlet (1) at the concentrated dust side, and enters the bag filter (III). When flux in the inorganic film cross-flow filter (II) is obviously decreased to the setpoint 20.6 m$^3$/m$^2$·h, the blowback system is automatically started up. The blowback gas (d) is the clean gas (b) that penetrates inorganic film filter (II) and is compressed with the compressor (V), and this stream of gas enters the inorganic film filter (II) for back washing via the blowback gas inlet (7); as a result, filter cake falls off and sinks down to the bottom of the separator; and then, the filter residue is automatically discharged through dust charge port (9).
C) After the clean gas (b) leaving the inorganic film cross-flow filter is condensed and rectified, the clean gas separates chloromethane gas (g) and methyl chlorosilane (h) so as to obtain product methyl chlorosilane (h) with purity of 99.99%; chloromethane gas (g) returns to the fluidized bed reactor to participate in the reaction.
D) The dust (e) trapped by the inorganic film filter (II) and bag filter (III) returns to the fluidized bed reactor (I) to participate in the reaction.

When blowback is performed, the blowback duration is 3 s and pressure is 0.2 MPa. The dust removal rate of gas mixture is up to 99.89% in this example.

Example 2

Dust and chloromethane enter a fluidized bed reactor, where reaction occurs to generate methyl chlorosilane gas mixture with the effect of catalyst copper powder; during the normal operation, the high-temperature flue gas is sent into the inorganic film cross-flow filter for separation with a centrifugal fan. The film filter element is of two pieces of single-tube alumina film with the pore diameter being 0.05 μm, inner diameter 8 mm, cross-flow velocity 25 m/s and film-crossing pressure differential 0.2 MPa. The dust content of the gas at the feed side is 2.9357 g/m$^3$; the dust content of the gas at the film penetration side is 2.6 mg/m$^3$. Partial gas mixture containing large-sized dust is sent into the bag filter with a fan; the purified gas leaving the inorganic film cross-flow filter separates chloromethane gas and methyl chlorosilane after passing through the condensation and rectification steps, and the obtained product methyl chlorosilane and chloromethane gases return to the fluidized bed reactor to participate in the reaction; the dust trapped by the inorganic film filter and bag filter returns to the fluidized bed reactor to participate in the reaction. The experiment is carried out for 20 hours and the film needs not to be blown back; the dust removal rate of gas mixture is up to 99.91% in this example.

Example 3

Silicon powder and chloromethane enter a fluidized bed reactor, where reaction occurs to generate methyl chlorosilane gas mixture with the effect of catalyst copper powder; the gas mixture containing silicon powder and copper powder is sent into the inorganic film cross-flow filter with centrifugal fan. A piece of a single prorus 316L tube is used, with the pore diameter being 5 μm, inner diameter 60 mm, cross-flow velocity 20 m/s, film-crossing pressure differential 0.08 MPa. The dust content of the gas at the feed side is 4.6293 $g/m^3$; the dust content of the gas at the film penetration side is 4.0 $mg/m^3$. Partial gas mixture containing large-sized dust is sent into the bag filter with a fan; the purified gas leaving the inorganic film cross-flow filter separates chloromethane gas and methyl chlorosilane after passing through the condensation and rectification steps, and the obtained product methyl chlorosilane and chloromethane gases return to the fluidized bed reactor to participate in the reaction; the dust trapped by the inorganic film filter and bag filter returns to the fluidized bed reactor to participate in the reaction. The experiment is carried out for 30 hours and the film needs not to be blown back; the dust removal rate of gas mixture is up to 99.91% in this example.

Example 4

Silicon powder and chloromethane enter a fluidized bed reactor, where reaction occurs to generate methyl chlorosilane gas mixture with the effect of catalyst copper powder; the high-temperature flue gas containing silicon powder and copper powder is sent into the inorganic film cross-flow filter with centrifugal fan. Film filter element is of a piece of a single prorus silicon carbide filter tube with the pore diameter being 10 μm, inner diameter 40 mm, outer diameter 60 mm, cross-flow velocity 15 m/s and film-crossing pressure differential 0.06 MPa. The dust content of the gas at feed side is 4.3684 $g/m^3$; the dust content of the gas at the film penetration side is 4.2 $mg/m^3$. Partial gas mixture containing large-sized dust is sent into the bag filter with a fan; the purified gas leaving the inorganic film cross-flow filter separates chloromethane gas and methyl chlorosilane after passing through the condensation and rectification steps, and the obtained product methyl chlorosilane and chloromethane gases return to the fluidized bed reactor to participate in the reaction; the dust trapped by the inorganic film filter and bag filter returns to the fluidized bed reactor to participate in the reaction. The experiment is carried out for 20 hours and the film needs not to be blown back; the dust removal rate of gas mixture is up to 99.90% in this example.

Example 5

Dust and chloromethane enter a fluidized bed reactor, where reaction occurs to generate methyl chlorosilane gas mixture with the effect of catalyst copper powder; the high-temperature flue gas containing silicon powder and copper powder is sent into the inorganic film cross-flow filter for separation with a centrifugal fan. Film filter element is of 6 pieces of single prorus symmetrical FeAl alloy film, with pore diameter being 20 μm, inner diameter 50 mm, cross-flow velocity 40 m/s, film-crossing pressure differential 0.02 MPa. The dust content of the gas at feed side is 3.2343 $g/m^3$, the dust content of the gas at the film penetration side is 4.2 $mg/m^3$. Partial gas mixture containing large-sized dust is sent into the bag filter with a fan; the clean leaving the inorganic film cross-flow filter is used as blowback gas for blowing back the film filter after being compressed with compressor; the remaining purified gas is condensed and rectified, and then is used to separate chloromethane gas and methyl chlorosilane, and the purity of the obtained product methyl chlorosilane is 99.95%; chloromethane gas returns to the fluidized bed reactor to participate in the reaction; the trapped dust returns to the fluidized bed reactor to participate in the reaction. The experiment is carried out for 20 hours and the film needs not to be blown back; the dust removal rate of gas mixture is up to 99.87% in this example.

Example 6

Dust and chloromethane enter a fluidized bed reactor, where reaction occurs to generate methyl chlorosilane gas mixture with the effect of copper catalyst; the high-temperature flue gas containing silicon powder and copper powder is sent into the inorganic film cross-flow filter for separation with a centrifugal fan. A piece of single symmetrical FeCrAl alloy film is used, with the pore diameter being 50 μm, inner diameter 60 mm, cross-flow velocity 20 m/s and film-crossing pressure differential 0.008 MPa. The dust content of the gas at the feed side is 2.2353 $g/m^3$; the dust content of the gas at the film penetration side is 3.8 $mg/m^3$. Partial gas mixture containing large-sized dust is sent into the bag filter with a fan; the clean leaving the inorganic film cross-flow filter is used as blowback gas for blowing back the film filter after being compressed with compressor; the remaining purified gas is condensed and rectified, and then is used to separate chloromethane gas and methyl chlorosilane, and the purity of the obtained product methyl chlorosilane is 99.94%; chloromethane gas returns to the fluidized bed reactor to participate in the reaction; the dust trapped by inorganic film filter and bag filter return to the fluidized bed reactor to participate in the reaction. The experiment is carried out for 30 hours and the film needs not to be blown back; the dust removal rate of gas mixture is up to 99.83% in this example.

The invention claimed is:
1. A method of dry dust removal in organic chlorosilane production comprising:
  delivering a high-temperature flue gas generated in a fluidized bed reactor to an inorganic film cross-flow filter with an air compressor to remove the dust for a first time;
  trapping a concentrated dust gas by the inorganic film cross-flow filter in a bag filter to remove the dust for a second time, wherein a gas mixture purified with the bag filter returns to the inorganic film cross-flow filter via a fan; and
  condensing a clean gas mixture passing through the inorganic film cross-flow filter in a condenser, the clean gas mixture then entering a rectifying column to separate chloromethane and methyl chlorosilane, wherein chloromethane returns to the fluidized bed reactor to participate in a reaction;

wherein the dust trapped by the inorganic film cross-flow filter and the bag filter returns to the fluidized bed reactor to participate in the reaction.

2. The dry dust removal method in organic chlorosilane production according to claim 1, wherein the inorganic film cross-flow filter includes a shell, a film filter element, an upper figured plate and a lower figured plate, of which the upper figured plate and the lower figured plate are placed in a middle of the shell, and the film filter element is placed between the upper figured plate and the lower figured plate; wherein a high-temperature flue gas inlet is provided at a top of the inorganic film cross-flow filter, a concentrated dust flue gas outlet is provided at a bottom of the filter, and a clean gas outlet and a blowback gas inlet are provided between the upper figured plate and the lower figured plate further wherein the high-temperature flue gas enters the inorganic film filter for cross-flow filtration via the high-temperature flue gas inlet, the clean gas passing through the inorganic film cross-flow filter is drained out via the clean gas outlet and the concentrated dust gas trapped by the inorganic film filter enters the bag filter via the concentrated dust gas outlet.

3. The dry dust removal method in organic chlorosilane production according to claim 2, wherein the inorganic film cross-flow filter is provided with a connection of a blowback device, the blowback gas is the clean gas passing through the inorganic film filter and compressed with a clean gas compressor, and enters the inorganic film filter for blowback cleaning via the blowback gas inlet, wherein, when a film flux is decreased to 40-60% of initial flux, the clean gas at the clean gas outlet of the inorganic film filter is automatically used to intermittently blow back the film separator and the filter cake attached on a film surface falls off and sinks down to the bottom of the separator, thus effectively preventing film pollution.

4. The dry dust removal method in organic chlorosilane production according to claim 1, wherein the high-temperature flue gas enters the inorganic film cross-flow filter in parallel to the film surface further wherein, when the gas enters the inorganic film cross-flow filter, the film-crossing pressure is controlled at 0.01 MPa-1 Mpa, and the flow rate on the film surface is 1 m/s-100 m/s.

5. The dry dust removal method in organic chlorosilane production according to claim 1, wherein the film filtering element is of a tubular film made of ceramics and metal material wherein a mean pore diameter of the film used is 0.02 μm~50 μm, and a diameter of film channel is 3-100 mm.

6. The dry dust removal method in organic chlorosilane production according to claim 5, wherein the ceramic material is at least one of aluminum oxide, zirconium oxide and silicon carbide, and the metallic material is at least one of stainless steel, FeAl alloy and FeCrAl alloy.

* * * * *